(12) United States Patent
Wang et al.

(10) Patent No.: US 8,766,020 B2
(45) Date of Patent: Jul. 1, 2014

(54) PROCESS FOR PRODUCING 2,3,3,3-TETRAFLUOROPROPENE

(75) Inventors: Haiyou Wang, Williamsville, NY (US); Hsueh Sung Tung, Getzville, NY (US); Rajiv R. Singh, Getzville, NY (US); Ian Shankland, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 737 days.

(21) Appl. No.: 12/510,740

(22) Filed: Jul. 28, 2009

(65) Prior Publication Data

US 2010/0029997 A1 Feb. 4, 2010

Related U.S. Application Data

(60) Provisional application No. 61/085,141, filed on Jul. 31, 2008.

(51) Int. Cl.
| | | |
|---|---|---|
| *C07C 17/25* | (2006.01) | |
| *C07C 19/08* | (2006.01) | |
| *C07C 21/18* | (2006.01) | |
| *C07C 21/00* | (2006.01) | |
| *C07C 17/00* | (2006.01) | |

(52) U.S. Cl.
USPC ............................................ 570/155; 570/153

(58) Field of Classification Search
None
See application file for complete search history.

(56) References Cited

U.S. PATENT DOCUMENTS

| | | |
|---|---|---|
| 5,895,639 A | 4/1999 | Swain et al. |
| 5,902,912 A | 5/1999 | Tung et al. |
| 7,135,601 B2 | 11/2006 | Mukhopadhyay et al. |
| 2007/0096053 A1 | 5/2007 | Nair et al. |
| 2007/0112230 A1 | 5/2007 | Mukhopadhyay et al. |
| 2007/0179324 A1 | 8/2007 | Van Der Puy et al. |
| 2007/0197842 A1 | 8/2007 | Mukhopadhyay et al. |
| 2008/0207962 A1 | 8/2008 | Rao et al. |
| 2010/0305370 A1 | 12/2010 | Devic et al. |

FOREIGN PATENT DOCUMENTS

| | | | |
|---|---|---|---|
| GB | WO2008075017 | 6/2008 | |
| GB | WO2009093047 | 7/2009 | |
| JP | WO2009084703 | 7/2009 | |
| WO | 9737955 A1 | 10/1997 | |
| WO | 9738958 A1 | 10/1997 | |
| WO | W02005037743 | 4/2005 | |
| WO | 2007056194 A1 | 5/2007 | |
| WO | 2007058836 A2 | 5/2007 | |
| WO | WO2007117391 | 10/2007 | |
| WO | W02008002499 | 1/2008 | |
| WO | W02008002501 | 1/2008 | |
| WO | WO2008012559 | * 1/2008 | ............ C07C 17/38 |
| WO | WO2008030440 | 3/2008 | |
| WO | 2008057794 A1 | 5/2008 | |
| WO | W02008060612 | 5/2008 | |
| WO | 2008075017 A2 | 6/2008 | |

OTHER PUBLICATIONS

Knunyants,I.L., et al.: "Reactions of Fluoro Olefins. XIII. Catalytic Hydrogenation of Perfluoro Olefins.": Izvestiya Akademii Nauk SSSR, Seriya Khimicheskaya 1412-18 Coden: IASKA6; ISSN: 0002-3353, 1960, XP002548816—pp. 1313, 1316.
Corresponding—First Office Action in Japanese Application No. 2009-179164, dated Oct. 1, 2013.

* cited by examiner

*Primary Examiner* — Clinton Brooks
(74) *Attorney, Agent, or Firm* — Bruce O. Bradford

(57) ABSTRACT

The present invention discloses a manufacturing process to produce high purity 1234yf from 245eb, which preferably includes the removal of impurities present in 245eb raw material, the dehydrofluorination of 245eb, and the removal of impurities present in final crude product. The disclosed manufacturing process allows the production of a 1234yf product with lower the levels of 1225ye and/or trifluoropropene, preferably in amounts of less than about 500, and 50 ppm, respectively.

17 Claims, No Drawings

US 8,766,020 B2

PROCESS FOR PRODUCING 2,3,3,3-TETRAFLUOROPROPENE

CROSS-REFERENCE TO RELATED APPLICATIONS

The present application claims the priority benefit of and incorporates herein by reference U.S. provisional application No. 61/085,141 filed Jul. 31, 2008. The present application also claims the priority benefit of as a continuation-in-part and incorporates herein by reference United States regular patent application Ser. No. 12/389,110, filed on Feb. 19, 2009, now U.S. Pat. No. 7,786,333, which in turn claims the priority benefit of U.S. regular application Ser. No. 11/588,464, filed Oct. 27, 2006, now U.S. Pat. No. 7,560,602, which in turn claims the priority benefit of U.S. provisional application No. 60/763,068, filed on Jan. 27, 2006 and 60/733,355, filed on Nov. 3, 2005, each of which is incorporated herein in its entirety by reference.

BACKGROUND

1. Field of Invention

The present invention relates to a processes for preparing 2,3,3,3-tetrafluoropropane (1234yf).

2. Related Art

Chlorine-containing compounds, such as chlorofluorocarbons (CFCs), have been employed as refrigerants, foam blowing agents, cleaning agents, solvents, heat transfer media, sterilants, aerosol propellants, dielectrics, fire extinguishing agents, and power cycle working fluids. Such chlorine-containing compounds have proven to be detrimental to the Earth's ozone layer. Many of the hydrofluorocarbons (HFCs), used as the substitutes of CFCs, have been found to contribute to global warming. For these reasons, there is a worldwide effort to develop new compounds that are more environmentally benign while at the same time being as effective, or more effective, from a performance standpoint.

Compositions containing fluorinated olefins, including particularly 2,3,3,3-tetrafluoropropene (1234yf), are among the materials being developed for use in the aforementioned applications. In addition, 2,3,3,3-tetrafluoropropene (1234yf) can be used as feedstock monomer for synthesis of fluoropolymers and macromolecular compounds.

Methods for the production of 1234yf are known. For example, U.S. Pat. No. 7,560,602, which is assigned to the assignee of the present invention and which is incorporated herein by reference, discloses a process for producing 2,3,3,3-tetrafluoropropene (1234yf) by catalytic dehydrofluorination of 1,1,1,2,3-pentafluoropropane (245eb). While this patent discloses a process having relatively high conversion and selectivity levels, and is therefore desirable and effective from the standpoint, applicants have nevertheless come to appreciate that several disadvantages are associated with processes of the type disclosed in this and similar patents. For example, the process disclosed in Example of 6 of this patent produces approximately three percent by weight of components that are described as being unknown. Applicants have come to appreciate that these byproducts can have a detrimental impact when used in connection with one or more of the applications mentioned above.

Applicants have also come to appreciate the presence of such undesireable materials in 2,3,3,3-tetrafluoropropene (1234yf) product can result, in at least certain cases, from the presence in the 1,1,1,2,3-pentafluoropropane (245eb) feedstock of certain impurities. More particularly, applicants have come to also appreciate that certain materials available as a source of 245eb include other components that contribute, when used as feed stock source for the production of 1234yf, to a reaction product composition containing high levels of contaminants, including trifluoropropene and 1,2,3,3,3-pentafluoropropene (1225ye). Applicants have come to appreciate that these and other materials can have a negative impact on the resulting product. For example, the aforementioned materials are undesirable in the 1234yf product because of their undesirably high level of toxicity.

Applicants have found, especially in view of the deficiencies noted above, improved processes for the production of 1234yf.

SUMMARY OF INVENTION

As mentioned above, applicants have found that for processes comprising dehydrofuoriniation of 245eb to form 2,3,3,3-tetrafluoropropene (1234yf), even a small amount of certain impurities in the reactor feed, and in particular in the 245eb feed stock, can have a significant negative impact on the desirability of resulting reaction product stream and/or 1234yf product, including particularly the purity of the resulting 1234yf. In particular embodiments, applicants have found that even small amounts of hexafluorinated propanes in the reactor feed, including particularly 1,1,1,2,3,3-hexafluoropropane (236ea), and/or pentafluorinated propenes, including particularly 1,2,3,3,3,-penatfluoropropene (1225ye), has a surprising and unexpectedly negative impact on the purity of the reaction product, and in particular the resulting 1234yf product.

Accordingly, one aspect of the invention provides methods for producing 1234yf, and preferably high purity 1234yf product, from 245eb comprising: (a) feeding at least one reactor feed stream containing 245eb to a least one dehydrofluorination reactor and (b) ensuring that said at least one feed stream contains not more than about 2% by weight, even more preferably not more than about 1% by weight, even more preferably not more than about 0.5% of any one of the compounds 1,1,1,2,3,3-hexafluoropropane (236ea) and 1,2,3,3,3,-penatfluoropropene (1225ye), based on the total weight of 245eb in the reactor feed stream(s).

In certain preferred embodiments, the methods comprise: providing a raw feed stock comprising at least about 50% by weight of 245eb and a minority of one or more impurities selected from unsaturated halocarbons, including particularly 1225ye and trifluoropropyne, 236ea, and 254eb; treating said raw feed stock, preferably by one or more of the steps of (i) subjecting said raw feed stock to a photochlorination process; (2) distilling said raw feed stock; and liquid-liquid extracting said raw feed stock, to produce a purified feed stock wherein said purified feed stock comprises a reduced amount of at least one of said impurities compared to said raw feedstock, preferably a reduced amount of the unsaturated halocarbon impurities compared to said raw feed stock; and subjecting said high purify feed stock to conditions effective to dehydrofluorinate at least a portion of said 1,1,1,2,3-pentafluoropropane to produce a reaction product comprising relatively more 2,3,3,3 tetrafluoropropene compared to said high purity feed stock.

In other embodiments, the methods comprise: providing a raw feed stock comprising 245eb and one or more impurities selected from, unsaturated halocarbons, including particularly 1225ye and trifluoropropyne, 236ea, and 254eb, and; optionally subjecting said raw feed stock to a photochlorination process to produce a modified feed stock comprising a reduced amount of at least one of said impurities compared to said raw feedstock, preferably a reduced amount of the unsaturated halocarbon impurities compared to said raw feed stock; purifying said raw feed stock or said modified feed stock to produce a high purify feed stock distillation and/or liquid-liquid extraction, wherein said high purity feed stock comprises relatively less impurities compared to said raw feed stock or said modified feed stock; subjecting said high purity feed stock to conditions effective to dehydrofluorinate at least a portion of said 1,1,1,2,3-pentafluoropropane to produce a reaction product comprising relatively more 2,3,3,3 tetrafluoropropene compared to said high purity feed stock.

In certain preferred embodiments, the methods of the present invention are carried out under conditions effective to produce a final product comprising a majority of 2,3,3,3-tetrafluoropropene, from 0 to about 500 part per million (ppm) of 1,2,3,3,3-pentafluoropropene and from 0 to about 50 ppm of trifluoropropyne, which conditions optionally but preferably include distilling said reaction product.

Another aspect of the invention provides a high purity 2,3,3,3-tetrafluoropropene (1234yf) product containing from trace amounts to less about 500 part per million (ppm) of 1,2,3,3,3-pentafluoropropene and from trace amounts to less than about 50 ppm of trifluoropropene.

Unless specifically indicated otherwise herein, all amounts identified herein by percentage refer to percent by weight.

DETAILED DESCRIPTION OF PREFERRED EMBODIMENTS OF THE INVENTION

The present invention can be generally described as a process for manufacturing high purity 1234yf from 245eb. As mentioned above, a critical step according to one aspect of certain embodiments of the invention comprises ensuring that the feed to the reactor in such a process contains not more than about 2% by weight of any one of the compounds 1,1,1,2,3,3-hexafluoropropane (236ea) and 1,2,3,3,3,-penatfluoropropene (1225ye), based on the total weight of 245eb in the reactor feed stream(s). Applicants contemplate that in many embodiments the ensuring step will involve treating a raw feedstock having an amount of one or more of these materials that is greater than the specified amount. However, it is also contemplated that in certain embodiments the ensuring step may comprise simply obtaining, for example from outside sources, a 245eb feedstock having less than the specified amount of the indicated materials.

According to certain preferred embodiments, the methods comprise the steps of:

(A) removal of impurities from the 245eb raw material (or raw feed stock) which, optionally but preferably, involves photochlorinating the unsaturates, such as 1225ye, present in the 245eb raw feed stock, preferably into 2,3-dichloro-1,1,1,2,3-pentafluoropropane, and/or involves distilling the 245eb feed to remove impurities such as 236 ea, 1225ye, 2,3-dichloro-1,1,1,2,3-pentafluoropropane, etc. to obtain a high purity 245eb feed, (B) dehydrofluorinating the high purity 245eb feed preferably in the presence of a caustic solution in liquid phase or a catalyst in vapor phase into 1234yf, and (C) optionally but preferably distilling the 1234yf reaction product to have a final product concentration of 1225ye that is below 500 ppm, preferably below 200 ppm, and more preferably below 100 ppm, and a final product concentration of trifluoropropyne that is below 50 pp.

A. The Removal of Impurities Included in 245eb Raw Material

In certain preferred embodiments, the unsaturated impurities such as 1225ye are converted, prior to entering the 245eb dehydrofluorination reactor, into corresponding saturated halogenated hydrocarbons having increased chlorine content, preferably via photochlorination in which chlorine ($Cl_2$) reacts with the unsaturated impurities in the presence of an ultraviolet light source. In one preferred photochlorination process, electromagnetic radiation, preferably light, from a suitable source is directed through a reactor wall to interact with the reactants therein. The source of light may be, for example, any one of a number of arc or filament lamps known in the art. Quartz or borosilicate glass such as Pyrex glass may be employed as transparent material to construct the portion of the reactor wall through which the light passes and enters the reactor. The photochlorination may be continuously carried out in the gas phase, in which starting materials are vaporized and contacted with chlorine vapor in a reaction zone. Although a wide range of chlorination reaction conditions are believed to be suitable, in certain preferred embodiments the reaction temperature is from about room temperature to about 50° C. Alternatively or additionally, the chlorination may be carried out in the liquid phase by feeding chlorine to a reactor containing starting materials, with it generally being preferred to control the reaction temperature below the boiling points of the starting materials and products.

The content of impurities such as 1225ye, 236ea, 254eb, and 2,3-dichloro-1,1,1,2,3-pentafluoropropane in the 245eb raw feed may be reduced by any means known in the art, such as extraction and preferably distillation. Although it is contemplated that a wide range of separation conditions can be used in accordance with the present invention, it is preferred in certain embodiments that the 245eb raw materials are distilled by passing at least a portion thereof through a standard distillation column and/or packed tower, or the like at atmospheric pressure, super-atmospheric pressure or a vacuum. Preferably the pressure is less than about 300 psig, more preferably less than about 150 psig and most preferably less than 100 psig. The pressure of the distillation column inherently determines the distillation operating temperature for a given degree of separation. The 245eb may be recovered as distillate by operating the distillation column at from about −10° C. to about 90° C., preferably from about 0° C. to about 80° C. Single or multiple distillation columns may be used. In certain preferred embodiments, the purity of 245eb after distillation is at least about 99.9% by weight.

B. The Dehydrofluorination of 245eb

The dehydrofluorination step can be carried out in a liquid phase in the presence of a caustic solution or in a gas phase in the presence of a dehydrofluorination catalyst. It is contemplated that the reaction can be carried out batch wise, continuous, or a combination of these.

One preferred converting step involves a reaction in which 245eb is contacted with a dehydrohalogenating agent, such as potassium hydroxide (KOH), sodium hydroxide (NaOH), $Ca(OH)_2$, CaO, and combinations of these and/or other catalysts, to form a reaction product comprising 2,3,3,3-tetrafluoropropene. This reaction may be described, by way of illustration but not necessarily by way of limitation, by the following reaction equation:

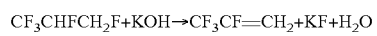

$$CF_3CHFCH_2F + KOH \rightarrow CF_3CF=CH_2 + KF + H_2O$$

In preferred aspects of such embodiments, the dehydrohalogenating agent comprises, and in certain embodiments consists essentially of, caustic material, such as KOH, and is preferably provided as an aqueous solution comprising from about 2% to about 100%, more preferably from about 5% to about 90%, and even more preferably from about 10% to about 80% by weight of the caustic material, preferably comprising or consisting essentially of KOH.

In certain preferred embodiments, the caustic solution, and preferably the KOH solution, is brought to a temperature of from about 20° C. to about 100° C., more preferably from about 30° C. to about 90° C., and most preferably from about 40° C. to about 80° C. The reaction pressure in such embodiments may vary, depending on particular processing parameters of each application. In certain embodiments, the reaction pressure ranges from atmospheric pressure, super-atmospheric pressure or under vacuum. The vacuum pressure, when used, preferably in certain embodiments ranges from about 5 torr to about 760 torr.

Another preferred converting step involves a reaction in which 245eb is contacted with a dehydrohalogenating catalyst, under conditions effective to form a reaction product comprising of 2,3,3,3-tetrafluoropropene and hydrogen fluoride. The dehydrofluorination reaction may be conducted in any suitable reaction vessel or reactor, but it should preferably be constructed from materials which are resistant to the corrosive effects of hydrogen fluoride such as nickel and its alloys, including Hastelloy, Inconel, Incoloy, and Monel. These may be single or multiple tubes packed with a dehydrofluorinating catalyst which may be one or more of halogenated metal oxides in bulk form or supported, metal halides in bulk form or supported, and carbon supported transition metals, metal oxides and halides. Suitable catalysts non-exclusively include fluorinated chromia ($Cr_2O_3$), fluorinated alumina ($Al_2O_3$), metal fluorides (e.g., $CrF_3$ and $AlF_3$) and carbon supported transition metals (zero oxidation state) such as Fe/C, Co/C, Ni/C, Pd/C or transition metals halides. In a preferred embodiment of the invention, the 245eb is pre-vaporized or preheated prior to entering the reactor. Alternatively, the 245eb is vaporized inside the reactor. Useful reaction temperatures may range from about 100° C. to about 600° C. Preferred temperatures may range from about 150° C. to about 450° C., and more preferred temperatures may range from about 250° C. to about 350° C. The reaction may be conducted at atmospheric pressure, super-atmospheric pressure or under vacuum. The vacuum pressure can be from about 5 torr to about 760 torr. Contact time of the 245eb with the catalyst may range from about 0.5 seconds to about 120 seconds, however, longer or shorter times can be used.

C. The Removal of Impurities Included in 1234yf crude product 2,3,3,3-tetrafluoropropene may be recovered from the reaction product mixture comprised of unconverted starting materials, product, and by-products including some or all of HF, 1234ze, 1225ye, and trifluoropropyne by any means known in the art, such as extraction and preferably distillation. In certain preferred embodiments, HF is removed or preferably recovered from the mixture of hydrogen fluoride and fluorocarbons prior to distillation. The removal of hydrogen fluoride may be realized via acid-base neutralization in a caustic solution scrubber. This may be conducted by running the product stream containing hydrogen fluoride and fluorocarbons through a caustic solution scrubber followed by a drying column. The recovering of hydrogen fluoride may be conducted in a gaseous phase by a continuous process of introducing a stream of sulfuric acid to a stream of fluorocarbon and hydrogen fluoride. This may be conducted in a standard scrubbing tower by flowing a stream of sulfuric acid countercurrent to a stream of fluorocarbon and hydrogen fluoride. Sulfuric acid extraction is described, for example in U.S. Pat. No. 5,895,639, which is incorporated herein by reference. The mixture of 2,3,3,3-tetrafluoropropene, unconverted 245eb and any other by-products are then passed through a distillation column. For example, the distillation may be preferably conducted in a standard distillation column at atmospheric pressure, super-atmospheric pressure or a vacuum. Preferably the pressure is less than about 300 psig, more preferably less than about 150 psig and most preferably less than 100 psig. The pressure of the distillation column inherently determines the distillation operating temperature. 2,3,3,3-tetrafluoropropene may be recovered as distillate by operating the distillation column at from about −10° C. to about 90° C., preferably from about 0° C. to about 80° C. Single or multiple distillation columns may be used. In certain preferred embodiments, the levels of undesired 1225ye and trifluoropropyne in the final 1234yf product may be below 500, and 50 ppm, respectively.

EXAMPLES

The following examples serve to demonstrate that high purity 1234yf can be produced through the process disclosed in the present invention.

Example 1

Purification of 245eb

A glassware set-up was used for purifying 245eb. The distillation flask was cooled with wet ice and was then charged with 3.00 kg of 88.1% 245eb crude feed. A couple of boiling chips were added into the flask to aid boiling. After reattaching the flask, the liquid was heated to cause distillation. The progress of the distillation was followed by measuring the temperature of the vapor at the top of fractionation column and by analyzing the compositions of periodically collected distillates. 245eb was collected during the period when its 245eb concentration was ≥99.9%. In the end, 1.73 kg of purified feed was obtained.

Example 2

245eb Dehydrofluorination in Caustic Solution

To a 50 gallon agitated reactor about 300 pounds of 245eb is charged into this vessel that contains a 20% molar excess of 25% KOH. A packed column with a condenser is also installed on top of the reactor, which is used to reflux the unreacted 245eb and relatively pure 1234yf is taken off at the exit of the condenser. The reaction is conducted at a temperature of 60° C. and the pressure is allowed to increase to about 190 psig and the product is taken off overhead as the reaction proceeds. Analysis of the product shows a 95.0% conversion of the 245eb and a selectivity of 96.9% to 1234yf.

Example 3

245eb Dehydrofluorination in the Presence of a Catalyst

A Monel tube reactor (0.75"OD×0.625"ID×23.0"L) was charged with 20 cc of catalyst pellets. The reactor was heated by a 12" split tube furnace. A multi-point thermocouple, inserted through catalyst bed, was used to measure the temperatures at the bottom of catalyst bed and at the top of catalyst bed. A purified 245eb feed (>99.9%) was passed through catalyst bed at a rate of 6 g/h (grams/hour). The effluent was analyzed by an on-line GC to determine 245eb conversion and 1234yf selectivity.

As shown in Table 1, the fluorinated $Cr_2O_3$ provided a 245eb conversion of about 99% and a selectivity of about 97% to 1234yf at 240-320° C., and the fluorinated MgO provided a 245eb conversion of about 98% and a selectivity of about 99% to 1234yf at 300-410° C.

TABLE 1

245eb dehydrofluorination over fluorinated metal oxide catalysts

| Catalyst | Temp. Bottom-Top (°) | Conversion 245eb (%) | Selectivity 1234yf (%) | Selectivity, others (%) |
|---|---|---|---|---|
| Fluorinated $Cr_2O_3$ | 240-320 | 98.9 | 96.9 | 3.1 |
| Fluorinated MgO | 300-410 | 97.8 | 98.8 | 1.2 |

Example 4

Purification of 1234yf

Approximately 100.0 lbs of 1234yf crude product is charged into a distillation still, which consists of a 10 gallon reboiler, 2 inch ID by 10 feet propack column, and a shell and tube condenser. The column has about 30 theoretical plates. The distillation still is equipped with temperature, pressure, and differential pressure transmitters. The distillation is run at a pressure of about 85 psig. The distillate is sampled and analyzed by GC at regular intervals. 1234yf is collected during the period when its 1234yf purity is ≥99.9%. In the end, 75.5 lbs of purified product is obtained. GC analysis of the final product indicates it contains 100 ppm of 1225ye and 10 ppm of trifluoropropyne.

What is claimed is:

1. A method for producing 2,3,3,3-tetrafluoropropene (1234yf) comprising:
   (a) providing a raw stream comprising 1,1,1,2,3-pentafluoropropane (245eb) and greater than about 2% by weight of each of 1,1,1,2,3,3-hexafluoropropane (236ea) and 1,2,3,3,3-pentafluoropropene (1225ye), based on the total weight of 245eb in the raw stream,
   (b) treating said raw stream to form a reactor feed stream such that the reactor feed stream contains not more than about 2% by weight of the compounds 1,1,1,2,3,3-hexafluoropropane (236ea) and 1,2,3,3,3-pentafluoropropene (1225ye), based on the total weight of 245eb in the reactor feed stream(s) wherein said treating comprises photochlorination; and
   (c) dehydrohalogenating said treated reactor feed stream to form 2,3,3,3-tetrafluoropropene (1234yf).

2. The method of claim 1 wherein said treating step comprises treating said raw stream such that it contains not more than about 0.5% by weight of at least one of the compounds 1,1,1,2,3,3-hexafluoropropane (236ea) and 1,2,3,3,3-pentafluoropropene (1225ye), based on the total weight of 245eb in the reactor feed stream(s).

3. The method of claim 1 wherein said method produces a 1234yf product comprising not more than about 500 part per million (ppm) of 1,2,3,3,3-pentafluoropropene and not more than about 50 ppm of trifluoropropyne.

4. The method of claim 1 wherein said treating step comprises treating said reactor feed stream such that it contains not more than about 1% by weight of either 1,1,1,2,3,3-hexafluoropropane (236ea) or 1,2,3,3,3,-penatfluoropropene (1225ye), based on the total weight of 245eb in the reactor feed stream(s).

5. A method for producing 2,3,3,3-tetrafluoropropene (1234yf) comprising:
   (a) providing a raw feed stock comprising a majority of 1,1,1,2,3-pentafluoropropane (245eb) and greater than about 2% by weight of 1,2,3,3,3-pentafluoropropene, and 1,1,1,2,3,3-hexafluoropropane;
   (b) treating said raw feed stock to produce a high purity feed stock, wherein said treating comprises photochlorination and wherein said high purity feed stock comprises not more than about 2% by weight of compound 1,1,1,2,3,3-hexafluoropropane (236ea) and 1,2,3,3,3-pentafluoropropene (1225ye), based on the total weight of 245eb;
   (c) subjecting said high purifly feed stock to conditions effective to dehydro fluorinate at least a portion of said 1,1,1,2,3-pentafluoropropane to produce a reaction product comprising more 2,3,3,3-tetrafluoropropene compared to the amount of said 2,3,3,3-tetrafluoropropene in said high purity feed stock; and
   (d) processing said reaction product to produce a final product comprising a majority of 2,3,3,3-tetrafluoropropene, and not greater than about 500 part per million (ppm) of 1,2,3,3,3-pentafluoropropene.

6. The method of claim 5 wherein said photochlorination comprises reacting at least a portion of said raw feed stock with $Cl_2$ in presence of ultraviolet light to yield 2,3-dichloro-1,1,1,2,3-pentafluoropropane.

7. The method of claim 5 wherein said high purity feed stream comprises at least about 99.9 weight percent 1,1,1,2,3-pentafluoropropane.

8. The method of claim 5 wherein said final product comprises from 0 to about 200 part per million of 1,2,3,3,3-pentafluoropropene.

9. The method of claim 5 wherein said final product comprises from 0 to about 100 part per million of 1,2,3,3,3-pentafluoropropene.

10. A method for producing 2,3,3,3-tetrafluoropropene (1234yf) comprising:
    (a) dehydrohalogenating 1,1,1,2,3,3-hexafluoropropane (236ea) to form a first composition comprising 1,2,3,3,3-pentafluoropropene (1225ye) and 1,1,1,2,3,3-hexafluoropropane (236ea);
    (b) hydrogenating said first composition to form a second composition comprising 1,1,1,2,3-pentafluoropropane (245eb) and greater than about 2% by weight of 1,1,1,2,3,3-hexafluoropropane (236ea) and 1,2,3,3,3-pentafluoropropene (1225ye),
    (c) treating said second composition to form a third composition having not more than about 2% by weight of 1,1,1,2,3,3-hexafluoropropane (236ea) and 1,2,3,3,3-pentafluoropropene (1225ye), based on the total weight of 245eb in the reactor feed stream(s) wherein said treating comprises photochlorination; and
    (d) dehydrohalogenating said third composition to form a product composition comprising 2,3,3,3-tetrafluoropropene (1234yf).

11. The method of claim 10 wherein said treating step comprises treating said second composition such that the third composition contains not more than about 1% by weight of 1,1,1,2,3,3-hexafluoropropane (236ea) and 1,2,3,3,3,-penatfluoropropene (1225ye), based on the total weight of 245eb in the reactor feed stream(s).

12. The method of claim 10 wherein said treating step comprises treating said second composition such that the third composition contains not more than about 0.5% by weight of compound 1,1,1,2,3,3-hexafluoropropane (236ea) and 1,2,3,3,3-pentafluoropropene (1225ye), based on the total weight of 245eb in the reactor feed stream(s).

13. The method of claim 10 wherein said photochlorination comprises reacting at least a portion of said second composition with $Cl_2$ in presence of ultraviolet light to yield 2,3-dichloro-1,1,1,2,3-pentafluoropropane.

14. The method of claim 10 wherein said third composition comprises at least about 99.9 weight percent 1,1,1,2,3-pentafluoropropane.

15. The method of claim 10 further comprising processing said product composition to produce a final product comprising a majority of 2,3,3,3-tetrafluoropropene, and not greater than about 500 part per million (ppm) of 1,2,3,3,3-pentafluoropropene.

16. The method of claim 15 wherein said final product comprises from 0 to about 200 part per million of 1,2,3,3,3-pentafluoropropene.

17. The method of claim 15 wherein said final product comprises from 0 to about 100 part per million of 1,2,3,3,3-pentafluoropropene.

* * * * *